United States Patent [19]

Ohnmacht

[11] Patent Number: 5,258,390
[45] Date of Patent: Nov. 2, 1993

[54] 9-(3 CYANOPHENYL) HEXAHYDRO-1,8 ACRIDINEDIONE

[75] Inventor: Cyrus J. Ohnmacht, Wilmington, Del.

[73] Assignee: Imperial Chemical Industries PLC, Millbank, United Kingdom

[21] Appl. No.: 963,798

[22] Filed: Oct. 20, 1992

[30] Foreign Application Priority Data

Oct. 21, 1991 [GB] United Kingdom ............... 9122305
Jun. 25, 1992 [GB] United Kingdom ............... 9213538

[51] Int. Cl.$^5$ ............................ C07D 219/08
[52] U.S. Cl. .................... 514/297; 546/103
[58] Field of Search ............... 514/297; 546/103

[56] References Cited

U.S. PATENT DOCUMENTS

| 3,454,577 | 7/1969 | Lehr et al. | 546/103 |
| 3,901,710 | 8/1975 | Ranz et al. | |
| 4,021,434 | 5/1977 | Murakami | 546/103 |
| 4,546,186 | 10/1985 | Abou-Gharbia | 546/102 |

FOREIGN PATENT DOCUMENTS

| 2003148 | 7/1971 | Fed. Rep. of Germany. |
| 2018738 | 10/1971 | Fed. Rep. of Germany. |
| 1575281 | 9/1980 | United Kingdom. |

OTHER PUBLICATIONS

S. M. Jain, et al. "Synthesis and Pharmacological screening of 1,8-dioxo-9-(substituted phenyl-)-1,2,3,4,5,6,7,8,9,10-decahydroacridines" *Ind. J. Chem.* (1991), 30B, 1037-1040.

H. Antaki "The Synthesis of Ethyl 4-Aryl-5,6,7,8-tetrahydro-5-oxo-quinoline-3-carboxylates and their Derivatives" *J. Chem. Soc.* (1963), 4877-4879.

Ibrahim Chaaban, et al. "Enaminones in the Mannich Reaction. Part 2. Further Investigations of Internal Mannich Reactions" *J. Chem. Soc., Perkin I* (1979), 1593-1596.

Magid Abou-Gharbiz "Synthesis of Novel Hexahydroquinolines and Hexahydroactridines" *Heterocycles* (1986), 5, 1347-1353.

*Primary Examiner*—Donald G. Daus
*Attorney, Agent, or Firm*—Thomas E. Jackson; James T. Jones

[57] ABSTRACT

The invention provides the novel compound, 9-(3-cyanophenyl)-3,4,6,7,9,10-hexahydro-1,8-(2H,5H)-acridinedione and pharmaceutically acceptable acid addition salts thereof, pharmaceutical compositions containing the compound, and the use of the compound in the treatment of urinary incontinence.

8 Claims, No Drawings

9-(3 CYANOPHENYL) HEXAHYDRO-1,8 ACRIDINEDIONE

This invention relates to a novel compound useful as a cell potassium channel opener in mammals such as man. More specifically, the invention relates to the specific compound 9-(3-cyanophenyl)-3,4,6,7,9,10-hexahydro-1,8-(2H,5H)acridinedione (shown as formula I on the formula page following this specification, and hereinafter referred to as "the compound"), its use in the treatment of urinary incontinence in mammals (including man), and pharmaceutical compositions containing it.

DE 2003148 discloses a group of 1,4-dihydropyridine derivatives which are said to display a wide and multifaceted pharmacological spectrum of action. The main effects said to be displayed by the compounds include strong muscular spasmoytic effects which become evident in the smooth musculature of the gastrointestinal tract, of the urogenital tract and of the respiratory system. Other main effects are stated to be on the heart (a "heart-relieving" effect) and in reducing the blood pressure of normotonic and hypertonic animals, so that they can be used as antihypertensive agents.

A novel compound has now been found that unexpectedly is capable of relaxing bladder smooth muscle tissue. This compound possesses further unexpected properties in that it is capable of acting selectively on the bladder without at the same time significantly affecting the cardiovascular system, as indicated by heart rate and blood pressure measurements. Thus the compound can advantageously be used to treat urinary incontinence in patients, such as the elderly, for whom cardiovascular effects, such as a hypotensive effect, are particularly undesirable.

This invention, as stated above, provides the compound 9-(3-cyanophenyl)-3,4,6,7,9,10-hexahydro-1,8-(2 H,5 H)acridinedione.

The invention also provides acid addition salts of the above compound made with sufficiently strong acids affording a physiologically acceptable anion.

The invention further provides a pharmaceutical composition comprising 9-(3-cyanophenyl)-3,4,6,7,9,10-hexahydro-1,8-(2 H,5 H)-acridinedione and a pharmaceutically acceptable diluent or carrier.

The invention further provides a method for the treatment of urinary incontinence without appreciably or significantly affecting blood pressure or heart rate, comprising administering to a mammal in need of such treatment an effective amount of the compound 9-(3-cyanophenyl)-3,4,6,7,9,10-hexahydro-1,8-(2 H,5 H)acridinedione.

The compound can be made by processes which include processes known in the chemical arts for the production of structurally analogous compounds. Such processes for its manufacture are provided as further features of the invention and are illustrated by the following procedures. If not commercially available, the necessary starting materials for the processes such as those described following may be made by procedures which are selected from standard organic chemical techniques, techniques which are analogous to the synthesis of known, structurally similar compounds, or techniques which are analogous to the above described procedure or the procedure described in the example. Such a process can be effected, generally, (a) by reacting a benzaldehyde of formula II, or an acetal or hemiacetal thereof, with ammonia or an ammonium salt (such as ammonium acetate) and 1,3-cyclohexanedione. The synthesis can be carried out along the lines reported by Abou-Gharbia in Heterocycles, 24 (5), 1347-1353, (1986), employing 3-cyanobenzaldehyde in place of the heterocyclic aldehyde used therein. Suitable reaction conditions are also reported by Antaki in J. Chem. Soc., 4877 (1963) and Ranz et al in U.S. Pat. No. 3,901,710.

(b) by reacting a compound of formula III with a corresponding benzaldehyde of formula II, or an acetal or hemiacetal thereof, or a reactive derivative thereof. The reaction can be conducted as reported by Chaaban et al. in J. Chem. Soc. Perkin I, 1593 (1978), or by Eynde et al, Tetrahedron, Vol 48, No. 7, pp1263-1268, 1992.

Reaction (a) is conveniently effected at a temperature in the range of from 0° to 100° C., preferably at an elevated temperature, for example in the range of from 35° to 90° C. Suitable solvents for the reaction include alcohols, for example, methanol or ethanol and carboxylic acids, for example acetic acid. The ammonia may, if desired, be employed in the form of ammonium hydroxide.

When benzaldehyde, or an acetal or hemiacetal thereof is used in reaction (b), the reaction is conveniently performed in the presence of an acid catalyst, for example hydrochloric acid, sulphuric acid, acetic acid or p-toluenesulphonic acid. Conveniently the reaction temperature is in the range of from 0° to 100° C., preferably from 25° to 40° C. Suitable solvents for the reaction include alcohols, for example ethanol.

When a reactive derivative of benzaldehyde is used in reaction (b), this may be, for example an N-(alpha-chlorophenylmethyl)pyridinium chloride. Thus, the benzaldehyde may be treated with thionyl chloride, and pyridine in the presence of a halogenated hydrocarbon solvent, such as dichloromethane, and the resultant N-(alpha-chlorophenylmethyl)pyridinium chloride may then be reacted with the compound of formula III.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the Examples.

When used to treat urinary incontinence, the compound is generally administered as an appropriate pharmaceutical composition which comprises the compound together with a pharmaceutically acceptable diluent or carrier, the composition being adapted for the particular route of administration chosen, with oral administration being preferred. Such compositions are provided as a feature of the invention. They may be obtained employing conventional procedures and excipients and binders and may be in a variety of dosage forms. For example, they may be in the form of tablets, capsules, solutions or suspensions for oral administration.

Treatment using a compound of the invention can be remedial or therapeutic as by administering a compound following the onset or development of urinary incontinence in a patient. Treatment can also be prophylactic or prospective by administering a compound in anticipation that urinary incontinence may develop, for example in a patient who has suffered from incontinence in the past.

According to another aspect, the invention provides the use of 9-(3-cyanophenyl)-3,4,6,7,9,10-hexahydro-1,8-(2 H,5 H)acridinedione or a pharmaceutically acceptable salt thereof in the manufacture of a medicoment for the treatment of urinary incontinence.

It is known that bladder tissue is excitable and that urinary incontinence can be caused by uncontrolled or unstable bladder contractions. It is further known that by functioning to open potassium channels, potassium channel opening compounds can thereby function to relax smooth muscle. While not wishing to be bound by theory, it is accordingly believed that the compound of this invention functions by opening potassium channels in bladder cells and thereby relaxing bladder smooth muscle tissue, thus preventing or ameliorating uncontrolled bladder contractions which can cause urinary incontinence.

The dose of the compound which is administered will necessarily be varied according to principles well known in the art taking account of the route of administration, the severity of the incontinence condition, and the size and age of the patient. In general, a compound of formula I will be administered to a warm blooded animal (such as man) so that an effective dose is received, generally a daily dose of above 0.005, for example in the range of about 0.01 to about 10 mg/kg body weight. Preferably the compound is administered orally in this dose range. It has been found that the compound is active and selective in rats when administered orally at a dose of 0.1, 0.3, 1.0 and 3.0 mg/kg. The compound has also been found to be active and selective in dogs when dosed orally at 3 mg/kg. It will be appreciated that the precise dose range at which the compound may be dosed to obtain a selective effect will depend upon the particular species to be treated. This dose range may be determined by conventional methods. In general, it is expected that a selective effect will be obtained when the compound is dosed orally at 3 mg/kg or below, for example at 1 mg/kg or below. In some cases, a selective effect may be obtained at 0.3 mg/kg or below, such as at 0.1 mg/kg or below.

It will be apparent to those skilled in the art that a compound of formula I can be co-administered with other therapeutic or prophylactic agents and/or medicaments that are not medically incompatible therewith. The compound of the invention does not show any indication of untoward side-effects in laboratory test animals at several multiples of the minimum effective dose.

The actions of the compound of formula I as a smooth muscle relaxant useful as a therapeutic agent for the treatment of urinary incontinence can be shown using suitably designed in vitro tests, such as the one described following. The compound according to the invention exhibits an $IC_{50}$ of $4.2 \pm 0.4$ micromolar in the test. "$IC_{50}$" is a well understood term and means the concentration of test compound which causes a 50% decrease in the in vitro contraction of the bladder tissue described in the following test.

Male albino Hartley guinea pigs (450–500 g) are sacrificed by cervical dislocation. The lower abdominal cavity is opened and the urinary bladder located. Once located, it is cleaned of surrounding connective and adipose tissue. The two pelvic nerves on the ventral surface of the bladder are cut away, then the bladder body is removed above the entrance of the ureters. The bladder is washed in Krebs-Henseleit buffer solution (composition (mM): NaCl 118.0, KCl 4.7, $MGSO_4$ 1.2, $KH_2PO_4$ 1.2, $CaCl_2$ 2.5, $NaHCO_3$ 25 and D-Glucose 11.1) and then placed on a buffer-soaked gauze in a petri dish. The dome of the bladder is cut off and discarded.

A mid-ventral longitudinal cut is made with scissors and the bladder laid flat on the gauze. Strips are cut from the dome edge and the base edge and discarded. The remaining detrusor mid-section is cut into two latitudinal (horizontal) strips, with an approximate width of 2.0 mm. These two strips are cut in half at the mid-dorsal section, creating four strips of similar dimensions. Each strip thus contains both dorsal and ventral portions of the bladder.

Each individual strip is tied at one end directly to a glass support rod and a length of 4–0 black braided silk suture is tied to the other end. The glass rods are secured in 20 ml tissue baths and the length of suture attached to a force-displacement transducer (Grass model FT03).

The tissues are bathed in Krebs-Henseleit buffer solution. The bathing solution is warmed to 37° C. and gassed with 5% $CO_2$ and 95% $CO_2$, with vigorous bubbling. The solution should have a pH value close to 7.4.

The transducers are connected to a polygraph (Grass model 7E) and interfaced with a Modular Instrument Micro 5000 signal processing system and Biowindow Data Acquisition Software (run on Microsoft OS/2 with an IBM-compatible PC).

The polygraph is calibrated at 5 mV/cm and calibration checked for linearity with weights of 5 and 0.5 grams.

The tissue is incubated in the buffer for 15 minutes without preload tension, then 30 minutes with tension applied. The preload tension applied is 2 grams that relaxes to approximately 1 gram. The tissue is washed at 15 minute intervals, with tension adjusted to 2 grams just prior to washing. After this 45 minute equilibration period, a priming dose of 15 mM KCl (total concentration in bath) is applied. The tissue is washed after 10 minutes and washed twice more at 15 minute intervals with tension adjusted to 2 grams before each washing.

When the tissue relaxes to a steady state after the final washing, 15 mM KCl is again dosed. Once the tissue reaches a steady state the base line data are acquired on the Biowindows Data Acquisition System. This is done by averaging 5 minutes of data, sampling at 32 Hz. Once the baseline is acquired, the experimental compounds are dosed in a cumulative manner in half log unit increments. The contact time for each dose is 10 minutes with the final 5 minutes being the period of time that the dose response data are acquired. If 30 $\mu$M of the test compound does not abolish detrusor mechanical activity, then 30 $\mu$M cromakalim is dosed to establish a maximum response. The effects of the compounds are expressed as % of maximum relaxation of agonist induced tension.

It will be further appreciated by those skilled in the art that the efficacy of compounds according to the invention can be demonstrated by standard assays in vivo. The following is a description of such a standard test which is used to evaluate smooth muscle relaxing capability of test compounds.

Male Wistar rats weighing 450–550 grams are anesthetized with 20 mg/kg, intraperitoneal (i.p.) Nembutal and 80 mg/kg, i.p. Ketamine. The trachea is cannulated to prevent airway obstruction. Body temperature is maintained by means of a heating pad. Arterial blood pressure and heart rate are measured with a pressure transducer connected to a polyethylene tube (PE 50) which has been inserted into the right carotid artery. The right jugular vein is cannulated for drug administration. The urinary bladder is exposed through a midline abdominal incision and emptied of urine by application of slight manual pressure. A catheter (PE 50) is inserted through the apex of the bladder dome around 3-4 mm into its lumen and tied with suture (4-0 silk) to prevent leakage. The bladder catheter is connected to a pressure transducer for the measurement of bladder pressure. The bladder is then placed back into the abdominal cavity and the incision is stitched closed except where the catheter exits the cavity. The bladder is allowed to equilibrate for approximately 15 minutes. After the equilibration period, the rats are infused with saline directly into the bladder at a rate of 0.05 ml/min for the entire time of the experiment. The bladder pressure is then monitored for the start of bladder contractions. When the contractions start, the animal is then allowed to stabilize its pattern of contractions around 30 to 45 minutes before drug administration.

The test compounds are given i.v. and the cutoff dose is 3 mg/kg. The reference drug cromakalim (Smithkline-Beecham) has been evaluated in this model and administered i.v. over the dose range of 0.05 to 0.5 mg/kg.

The above in vivo assay enables an assessment of both the blood pressure and cystometric activity of test compounds. Blood pressure is measured immediately after drug injection and at 5, 15 and 30 minutes later. Micturition contractions are induced by a slow continuous infusion of saline directly into the bladder. The average change (in seconds from control) in the duration of the intercontraction interval (the time between contractions) over an approximate 20-min period is reported for each compound.

The following is a description of a test in vivo which is complimentary to the above described tests and which can be used to ascertain if a test compound is active and, additionally, if the test compound exhibits selectivity for the bladder without significant cardiovascular effects when dosed orally. The compound is active and selective in this test when dosed orally at 0.1, 0.3, 1.0 and 3.0 mg/kg body weight.

Male Wistar rats (400-500 g) were anesthetized with 50 mg/kg Nembutal, i.p. For each rat, the abdominal region and the front and back of the neck were shaved and povidone-iodine was applied to the skin. For carotid catheterization, the left carotid artery was exposed via a small ventral cervical incision. The exposed area was flushed with a 2% lidocaine HCl solution to relax the vessel. The catheter, filled with 0.9% saline, was introduced approximately 2.4 cm into the artery so that its tip resided in the aortic arch. The distal end of the catheter was exteriorized at the nape of the neck, filled with heparin (1000 units/ml) and heat sealed. For bladder catheterization, the bladder was exposed through a midline abdominal incision. A trocar was passed through the abdominal muscle about 1 cm from the upper end of the incision and then tunneled subcutaneously to emerge through the skin at the back of the neck. A saline-filled catheter was passed through the trocar. A small opening in the bladder dome was created with an Accu-Temp cautery. The catheter was placed into the bladder and secured with a 4-0 silk ligature. The catheter was flushed with saline and patency was noted. The external end of the catheter was heat-sealed to prevent urine leakage. The abdominal muscles and the skin were sutured. Both catheters were threaded through a stainless steel anchor button (Instech), which was then sutured to the subcutaneous muscle at the point of exteriorization. The skin was sutured closed over the button. The animals were allowed to recover from anesthesia.

24-48 hours after surgery, each rat was placed in a metabolism cage and connected via the anchor button to an Instech spring tether and swivel system to protect the catheters from damage and to allow the animal free movement in the cage. The carotid catheter was connected to a Gould P23XL pressure transducer for blood pressure measurement. The bladder catheter was connected to a pump for saline infusion and to a pressure transducer by means of PE50 tubing and a 4-way stopcock. A toploading balance with a collection cup was placed under the cage for urine output measurement.

The rats were weighed, orally sham-dosed (dosing needle introduced, but no fluid expelled), and transvesical saline infusion (0.18 ml/min) was begun and continued throughout the experiment. Variations in blood pressure, heart rate, intravesical pressure and urine output were recorded on either a Grass Polygraph or a Gould TA4000 recording system. The animals were allowed to equilibrate until the micturition pattern became consistent (approx. 45-90 min.). At this point, a basal level of each experimental parameter was recorded and the rats were administered by oral gavage the appropriate dose of compound (in a 75% PEG 400—saline vehicle) in concentrations such that the volume was 1 ml/kg body weight. The effects of the compounds on experimental parameters were followed for five hours after administration.

Experimental results for both the interval between contractions and also heart rates were expressed as the mean ±S.E.M. (Standard Error of Measures) % change from basal level, with each animal serving as its own control. Mean arterial pressure is expressed as mean ±S.E.M mm Hg change from basal level.

It is further noted that the compound also exhibits activity and selectivity when tested in vivo in a dog model.

Well trained, conscious female beagles are catheterized with a sterile foley catheter and drained of residual urine. Utilizing a four way stopcock, the catheter is connected to a Grass Model pressure transducer, and bladder pressure is recorded on a dynograph. The beagles are surgically implanted with chronic indwelling carotid artery catheters. When connected to pressure transducers and a recorder, the carotid artery catheter allows for the simultaneous monitoring of blood pressure and heart rate along with bladder pressure obtained from the acute indwelling foley bladder catheter.

Following a 15 minute equilibration period, sterile saline is infused into the bladder via the 4 way stopcock in 30 ml bolus injections, until a sustained rise in bladder pressure (10-12 mmHg) is observed. This is followed by a series of smaller (10-15 ml) bolus infusions, until spontaneous bladder contractions begin. Total infusion volume ranges from approximately 100 ml to 200 ml depending upon the individual animal. Simultaneously, base line systolic and diastolic blood pressure as well as heart rate are obtained. A control period of continuous spontaneous bladder contractions is recorded for 30 to 60 minutes to establish a baseline measurement of the interval between contractions (Intercontraction Interval, Seconds) and to estimate the number of bladder contractions per hour.

Test compounds are then given in a suspension of Aqueous Suspending Vehicle by oral gavage. Blood pressure is measured continuously, with heart rate measurements determined every fifteen minutes for the first two hours after dosing, and every thirty minutes for the third and fourth hours. Bladder pressure and intercontraction intervals are followed for four hours following oral dosing.

Each dog is allowed at least one week for recovery between experiments. Only calm and cooperative dogs are chosen for training and acclimation to light restraint and bladder catheterization. No animals exhibiting distress or discomfort as a result of the procedures are utilized for this model.

The compound was active and selective in this test when administered at a dose of 3 mg/kg.

The invention will now be illustrated by the following example in which, unless stated otherwise:

(i) temperatures are given in degrees Celsius (C.); operations were carried out at room or ambient temperature, that is, at a temperature in the range of 18°–25°;

(ii) melting points are uncorrected and (d) indicates decomposition; the melting points given are those obtained for the materials prepared as described; polymorphism may result in isolation of materials with different melting points in some preparations;

(iii) all final products were essentially pure by TLC and had satisfactory nuclear magnetic resonance (NMR) spectra and microanalytical data;

(iv) yields are given for illustration only;

(v) chemical symbols have their usual meanings; the following abbreviations have also been used: v (volume), w (weight); mp (melting point), L [liter(s)], mL (milliliters), mmol (millimoles), g [gram(s)], mg [milligram(s)], min (minutes), h (hour); and (vi) NMR data is in the form of delta values given in parts per million (ppm) relative to trimethylsilane (TMS) as an internal standard, determined at 300 MHz using $d_6$-dimethylsulfoxide as solvent; conventional abbreviations for signal shape are used.

(vii) mass spectra (MS) were run with an electron energy of 70 electron volts in the chemical ionization mode using a direct exposure probe; only the parent mass in reported.

EXAMPLE 1

9-(3-Cyanophenyl)-3,4,6,7,9,10-hexahydro-1,8-(2 H,5 H)acridinedione

A stirred mixture of 3-cyanobenzaldehyde (1.48 g), 1,3-cyclohexanedione (2.53 g) and ammonium acetate (1.24 g) in ethanol (20 mL) was refluxed for 18 hours. The mixture was poured into water, and the yellow solid collected and dried under vacuum to yield the title acridinedione (3.22 g); mp 285°–288° C.; NMR: 1.80-1.93 (m,4) 2.19–2.22 (m,4) 2.50–2.54 (m,4) 4.91 (s,1) 7.37–7.42 (m,1) 7.48–7.54 (m,3) 9.55 (s,1); MS: m/z=319 (M+1).

Analysis for $C_{20}H_{18}N_2O_2$:
Calculated: C, 75.44; H, 5.71; N, 8.80.
Found: C, 75.27; H, 5.66; N, 8.77.

EXAMPLE 2

9-(3-Cyanophenyl)-3,4,6,7,9,10-hexahydro-1,8-(2 H,5 H)-acridinedione

To a stirred mixture of 3-amino-2-cyclohexen-1-one (4.45g) and 25 ml of ethanol was added 32mL of 1N HCl, followed by 3-cyanobenzaldehyde (2.62 g), and the mixture stirred at ambient temperature overnight. The resulting solid was filtered off, washed well with water and then ethanol. After drying at 50° C./0.2 torr the title compound was obtained as a pale yellow solid (3.89 g), mp 303–7° C. dec MS (CI, $CH_4$): 319 (M+1).

Analysis for $C_{20}H_{18}N_2O_2$:
Calculated: C; 75.44; H, 5.71; N, 8.80.
Found: C, 75.42; H, 5.70; N, 8.66.

The nmr spectra was identical to that of the product of Example 1.

EXAMPLE 3

9-(3-Cyanophenyl)-3,4,6,7,9,10-hexahydro-1,8-(2 H,5 H)-acridinedione

A stirred solution of thionyl chloride (2.86 g) in 24 mL of methylene chloride, under nitrogen, was cooled in a −10° C. bath and treated with a solution of pyridine (1.90g) in 12mL of methylene chloride as a slow stream. A solution of 3-cyanobenzaldehyde (2.62 g) in 10 mL of methylene chloride was then added as a slow stream and the mixture stirred in the bath at −10° to 0° C. for 1 hour. 3-Amino-2-cyclohexen-1 -one (6.67 g) was then added in one portion and was washed in with 10 mL of methylene chloride. After stirring at ambient temperature overnight the methylene chloride solvent was removed in vacuo and the resulting orange solid triturated with water. The solids were collected by suction filtration, washed well with water and then ethanol, and then dried in vacuo at 60° C./0.2 torr, to afford the title compound (3.86 g) as a pale yellow solid; mp. 302°–5° C. dec. MS (CI, $CH_4$): 319 (M+1). The nmr spectrum was identical to that of the product of Example 1.

EXAMPLE 4

The following illustrate representative pharmaceutical dosage forms containing the compound for therapeutic or prophylactic use in humans:

|  | mg/tablet |
|---|---|
| (a) Tablet | |
| The compound | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b) Capsule | |
| The Compound | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

FORMULAE

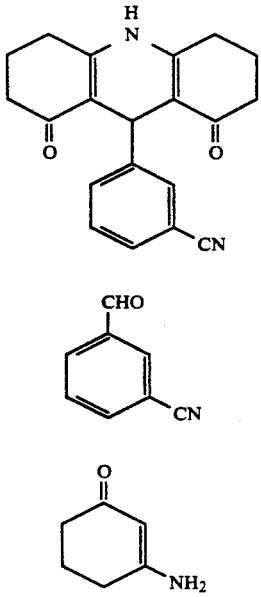

I claim:

1. 9-(3-cyanophenyl)-3,4,6,7,9,10-hexahydro-1,8-(2 H,5 H)-acridinedione, or a pharmaceutically acceptable acid addition salt thereof.

2. A compound as claimed in claim 1, which is 9-(3-cyanophenyl)-3,4,6,7,9,10-hexahydro-1,8-(2 H,5 H)-acridinedione.

3. A pharmaceutical composition comprising a compound as claimed in claim 1 or claim 2, and a pharmaceutically acceptable diluent or carrier.

4. A method for the treatment of urinary incontinence without appreciably or significantly affecting blood pressure or heart rate, comprising administering to a mammal in need of such treatment an effective amount of a compound as claimed in claim 1 or claim 2.

5. A method as claimed in claim 4, in which said compound is administered orally.

6. A method for the treatment of urinary incontinence, which comprises orally administering to a mammal in need of such treatment from about 0.01 to about 10 mg/kg body weight of a compound as claimed in claim 1 or claim 2.

7. A method as claimed in claim 6, in which the amount of said compound administered is at or below 3 mg/kg body weight.

8. A method for inhibiting bladder contractions in a mammal, which comprises administering an effective amount of a compound as claimed in claim I or claim 2.

* * * * *